United States Patent
Wächtler et al.

(10) Patent No.: US 6,177,594 B1
(45) Date of Patent: Jan. 23, 2001

(54) 4-(4-OXOCYCLOHEXYL) BENZAMIDES AS INTERMEDIATE PRODUCTS FOR MEDICAMENTS

(75) Inventors: Andreas Wächtler, Tubingen; Margit Stern, Darmstadt; Volker Reiffenrath, Rossdorf, all of (DE)

(73) Assignee: Merck Patent Gesellschaft mit beschrankter Haftung, Darmstadt (DE)

( * ) Notice: Under 35 U.S.C. 154(b), the term of this patent shall be extended for 0 days.

(21) Appl. No.: 09/202,135
(22) PCT Filed: Jun. 24, 1997
(86) PCT No.: PCT/EP97/03299
 § 371 Date: Dec. 9, 1998
 § 102(e) Date: Dec. 9, 1998
(87) PCT Pub. No.: WO98/01420
 PCT Pub. Date: Jan. 15, 1998

(30) Foreign Application Priority Data

Jul. 3, 1996 (DE) .............................. 196 26 771

(51) Int. Cl.[7] .................. C07C 233/65; C07C 231/02
(52) U.S. Cl. .................. 564/169; 514/621; 540/200; 546/226; 548/539; 548/966; 564/134; 564/138; 564/148
(58) Field of Search .................. 564/169, 134, 564/142, 138; 514/621; 540/200; 546/226; 548/539, 966

(56) References Cited

U.S. PATENT DOCUMENTS 5,454,974 * 10/1995 Boller et al. ............... 252/299.61

FOREIGN PATENT DOCUMENTS 0331933    9/1989  (EP) .

OTHER PUBLICATIONS

EP331933–English Abstract, 1989.

* cited by examiner

Primary Examiner—Shailendra Kumar
(74) Attorney, Agent, or Firm—Millen, White, Zelano & Branigan, P.C.

(57) ABSTRACT

Benzamides of the formula I:

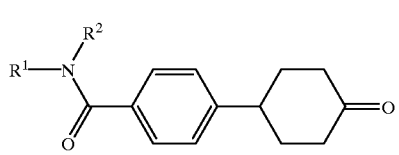

wherein
$R^1$ and $R^2$ independently of one another are each alkyl having 1–6 C atoms, or
$R^1$ and $R^2$ together are alkylene,
and their salts,
are suitable as intermediates in the synthesis of drugs.

15 Claims, No Drawings

4-(4-OXOCYCLOHEXYL) BENZAMIDES AS INTERMEDIATE PRODUCTS FOR MEDICAMENTS

This application is a 371 of PCT/EP/97/03299, filed Jun. 24, 1997.

The invention relates to benzamides of the formula I:

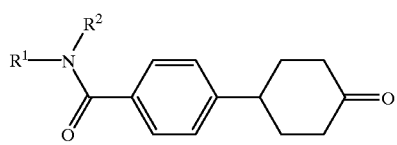

wherein
$R^1$ and $R^2$ independently of one another are each alkyl having 1–6 C atoms, or
$R^1$ and $R^2$ together are alkylene, and their salts.

The object of the invention was to find novel compounds which can be used especially as intermediates in the synthesis of drugs, but which can also be used directly for the preparation of drugs.

It has been found that the compounds of the formula I and their salts are important intermediates for the preparation of drugs.

The invention provides the benzamide derivatives of the formula I and their salts.

Above and below, the radicals $R^1$ and $R^2$ are as defined in the formulae I to III, unless expressly indicated otherwise.

In the above formulae, alkyl is preferably unbranched and has 1, 2, 3, 4, 5 or 6 C atoms, preferably 1, 2, 3, 4 or 5 C atoms; it is preferably methyl, ethyl or propyl, other preferences being isopropyl, butyl, isobutyl, sec-butyl or tert-butyl as well as n-pentyl, neopentyl or isopentyl.

Alkylene is preferably, ethylene, propylene, butylene or pentylene.

The invention also provides a process for the preparation of benzamides of the formula I according to claim 1 and their salts, characterized in that a compound of the formula II:

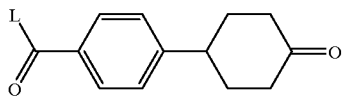

wherein
L is Cl, Br, OH or a reactive esterified OH group, is reacted with a compound of the formula III:

HNR$^1$R$^2$    III or one of its salts,
wherein $R^1$ and $R^2$ are defined as indicated, and/or
in that a base of the formula I is converted to one of its salts by treatment with an acid.

Incidentally, the compounds of the formula I and also the starting materials for their preparation are prepared by methods known per se, such as those described in the literature (e.g. in the standard works like Houben-Weyl, Methoden der organischen Chemie (Methods of Organic Chemistry), Georg-Thieme-Verlag, Stuttgart), under reaction conditions which are known and suitable for said reactions. It is also possible here to make use of variants known per se, which are not mentioned in greater detail in this specification.

If desired, the starting materials can also be formed in situ so that they are not isolated from the reaction mixture but immediately reacted further to give the compounds of the formula I.

In the compounds of the formulae II, the radical L is preferably Cl or Br; however, it can also be I, OH or a reactively modified OH group such as alkylsulphonyloxy having 1–6 C atoms (preferably methylsulphonyloxy) or arylsulphonyloxy having 6–10 C atoms (preferably phenylsulphonyloxy, p-tolylsulphonyloxy or 1- or 2-naphthalenesulphonyloxy).

The methods used for reacting the compounds of the formulae II with compounds of the formulae III are those known from the literature for the acylation of amines. The components can also be melted together, optionally in a sealed tube or in an autoclave, without the presence of a solvent.

The compounds of the formula III can also be used in the form of their salts, as described for example by Davidson et al., Synthetic Commun. 20, 727–732 (1990).

However, the compounds can also be reacted in the presence of an inert solvent.

Examples of suitable inert solvents are hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl ether or monoethyl ether (methyl glycol or ethyl glycol) or ethylene glycol dimethyl ether (diglyme); ketones such as acetone or butanone; amides such as acetamide, dimethylacetamide or dimethylformamide (DMF); nitriles such as acetonitrile; sulphoxides such as dimethyl sulphoxide (DMSO); carbon disulphide; nitro compounds such as nitromethane or nitrobenzene; esters such as ethyl acetate; and optionally also mixtures of said solvents with one another or mixtures with water.

It may be favourable to add an acid-binding agent, for example an alkali metal or alkaline earth metal hydroxide, carbonate or bicarbonate or another alkali metal or alkaline earth metal salt of a weak acid, preferably the potassium, sodium or calcium salt of a weak acid, or to add an organic base such as triethylamine, dimethylamine, pyridine or quinoline or an excess of the amine component. The reaction time is between a few minutes and 14 days, depending on the conditions applied; the reaction temperature is between −20 and 1000, normally between −10 and 40°.

A base of the formula I can be converted with an acid to the corresponding acid addition salt, for example by reacting equivalent amounts of the base and the acid in an inert solvent such as ethanol, and then evaporating the solution. Acids which are particularly suitable for this reaction are those which produce biocompatible salts. Thus it is possible to use inorganic acids, e.g. sulphuric acid, nitric acid, hydrohalic acids such as hydrochloric acid or hydrobromic acid, phosphoric acids such as orthophosphoric acid, or sulphamic acid, and organic acids, especially aliphatic, alicyclic, araliphatic, aromatic or heterocyclic monobasic or polybasic carboxylic, sulphonic or sulphuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulphonic or ethanesulphonic acid, ethanedisulphonic acid, 2-hydroxy-ethanesulphonic acid, benzenesulphonic acid, p-toluene-sulphonic acid, naphthalenemonosulphonic and naphthalene-disulphonic acids or laurylsulphuric acid. Salts with non-biocompatible acids, e.g. picrates, can be used to isolate and/or purify the compounds of the formula I.

On the other hand, compounds of the formula I can be converted with bases (e.g. sodium or potassium hydroxide or carbonate) to the corresponding metal salts, especially alkali metal or alkaline earth metal salts, or to the corresponding ammonium salts.

The invention also provides the use of the compounds of the formula I as intermediates for the synthesis of drugs.

The invention also provides the use of the compounds of the formula I according to claim 1 in reduction reactions, characterized in that the reaction of the compounds of the formula I is carried out with complex metal hydrides.

The reduction of the ketoamides according to the invention can be carried out e.g. with lithium aluminium hydride, analogously to the method of Deslongchamps et al., Can. J. Chem., 53, 3613–3619 (1975).

Examples of other reducing agents which can be used are $NaBH_4$ or $NaAl(OCH_2CH_2OCH_3)_2H_2$, as well as diborane, if desired with the addition of catalysts such as $BF_3$, $AlCl_3$ or LiBr. Examples of suitable solvents are the inert solvents mentioned above.

Above and below, all temperatures are given in ° C. "Conventional working-up" has the following meaning in the Examples below: Water is added, if necessary, the pH is adjusted to between 2 and 10, if necessary, depending on the constitution of the end product, the mixture is extracted with ethyl acetate or dichloromethane, the phases are separated, the organic phase is dried over sodium sulphate and evaporated and the residue is purified by chromatography on silica gel and/or by crystallization. Rf values on silica gel.

EXAMPLE 1

4-(4-Oxocyclohexyl)benzoyl chloride [obtainable by reacting 0.75 mol (130.7 g) of 4-phenylcyclohexanone with 1 mol of oxalyl chloride and 2 mol of $AlCl_3$ in dichloromethane, followed by hydrolysis with ice-water/HCl] is added to an aqueous solution (15%) of 3 mol of dimethylamine and the mixture is stirred for 2 hours at 0 to 5°. It is worked up in conventional manner to give 125.2 g of N,N-dimethyl-4-(4-oxocyclohexyl)benzamide, m.p. 118°; yield: 68% based on 4-phenylcyclohexanone.

EXAMPLE 2

Equivalent amounts of (4-oxocyclohexyl)benzoyl chloride and dimethylamine hydrochloride are dissolved in dichloromethane. An equivalent amount of triethylamine is then added and the mixture is stirred for 3 hours.

N,N-dimethyl-4-(4-oxocyclohexyl)benzamide, m.p. 118°, is obtained after conventional working-up.

What is claimed is:

1. A benzamides of the formula I:

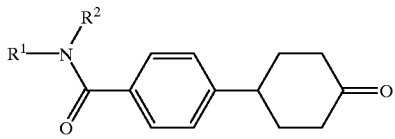

wherein
$R^1$ and $R^2$ independently of one another are each alkyl having 1–6 C atoms, or
$R^1$ and $R^2$ together are alkylene; or
a salt thereof.

2. A compound according to claim 1, wherein said compound is N,N-Dimethyl-4-(4-oxocyclohexyl) benzamide or a salt thereof.

3. A process for the preparation of a benzamide of formula I, or a salt thereof, according to claim 1, comprising:
reacting a compound of the formula II:

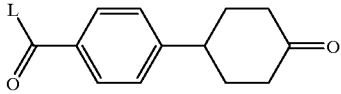

wherein
L Is Cl, Br, OH or a reactive esterified OH group, with a compound of the formula III:

$HNR^1R^2$   III or a salt thereof,
wherein $R^1$ and $R^2$ are defined as indicated; and/or
a base of the formula I is converted to one of its salts by treatment with an acid.

4. In a method of synthesizing a drug compound, the improvement wherein a compound of the formula I, or salt thereof, according to claim 1 is used as an intermediate.

5. A process comprising reducing a compound of the formula I according to claim 1 by reaction with a complex metal hydride.

6. A compound according to claim 1, wherein $R^1$ and $R^2$ are each independently alkyl having 1–6 C atoms or together are ethylene, propylene, butylene or pentylene.

7. A compound according to claim 6, wherein $R^1$ and $R^2$ together are ethylene, propylene, butylene or pentylene.

8. A compound according to claim 6, wherein $R^1$ and $R^2$ are each, independently, methyl, ethyl, propyl, isopropyl, butyl, isobutyl, sec-butyl, tert-butyl, n-pentyl, neopentyl, or isopentyl.

9. A process for the preparation of a benzamide of formula I, or salt thereof, according to claim 6 comprising:
reacting a compound of the formula II:

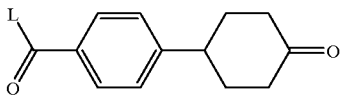

wherein
L Is Cl, Br, OH or a reactive esterified OH group, with a compound of the formula III:

$HNR^1R^2$  III or salt thereof, wherein $R^1$ and $R^2$ are defined as indicated; and/or a base of the formula I is converted to one of its salts by treatment with an acid.

10. In a method of synthesizing a drug compound, the improvement wherein a compound of the formula I, or salt thereof, according to claim 6 is used as an intermediate.

11. A process comprising reducing a compound of the formula I according to claim 6 by reaction with a complex metal hydride.

12. A process according to claim 5, wherein said complex metal hydride is lithium aluminum hydride.

13. A process according to claim 11, wherein said complex metal hydride is lithium aluminum hydride.

14. A compound according to claim 1, wherein $R^1$ is ethyl, propyl, isopropyl, butyl, isobutyl, sec-butyl, tert-butyl, n-pentyl, neopentyl, isopentyl, or together with $R^2$ is ethylene, propylene, butylene or pentylene.

15. A compound according to claim 1, wherein $R^2$ is ethyl, propyl, isopropyl, butyl, isobutyl, sec-butyl, tert-butyl, n-pentyl, neopentyl, isopentyl, or together with $R^1$ is ethylene, propylene, butylene or pentylene.

\* \* \* \* \*